United States Patent [19]
Braiman et al.

[11] Patent Number: 5,980,831
[45] Date of Patent: Nov. 9, 1999

[54] SUPPORT PLANAR GERMANIUM WAVEGUIDES FOR INFRARED EVANESCENT-WAVE SENSING

[76] Inventors: Mark S. Braiman, 1618 Shady Grove Ct., Charlottesville, Va. 22902-7218; Susan E. Plunkett, 2613 Waldo La., Richmond, Va. 23228-6019; James J. Stone, 301-A Valley Rd. Extended, Charlottesville, Va. 22903

[21] Appl. No.: 08/874,711

[22] Filed: Jun. 13, 1997

Related U.S. Application Data

[60] Provisional application No. 60/019,969, Jun. 17, 1996.

[51] Int. Cl.$^6$ ..................................................... G01N 21/00
[52] U.S. Cl. .......................... 422/82.11; 385/131; 385/12
[58] Field of Search ....................... 422/82.11; 385/123, 385/129–132, 12; 250/339.12

[56] References Cited

U.S. PATENT DOCUMENTS

| | | | |
|---|---|---|---|
| 3,898,605 | 8/1975 | Burns | 250/338 |
| 4,169,676 | 10/1979 | Kaiser | 356/39 |
| 4,372,642 | 2/1983 | Singer et al. | 350/96.12 |
| 5,082,629 | 1/1992 | Burgess, Jr. et al. | 422/82.11 |
| 5,272,518 | 12/1993 | Vincent | 356/405 |
| 5,750,410 | 5/1998 | Dou et al. | 422/82.11 |

OTHER PUBLICATIONS

Design for Supported Planar Waveguides for Obtaining Mid–IR Evanescent–Wave Absorption Spectra from Biomembranes of Individual Cells, Mark S. Braiman and Susan E. Plunkett, vol. 51, No. 4, Apr. 1997, Applied Spectroscopy, pp. 592–597.

Mid–IR evanescent–wave absorption spectra of thin films and coatings measured with a ~50–um–thick planar Ge waveguide sensors, James J. Stone, Mark S. Braiman and Susan E. Plunkett, Published Jun. 15, 1997, Process SPIE.

*Primary Examiner*—Jeffrey Snay
*Attorney, Agent, or Firm*—Sheldon H. Parker

[57] ABSTRACT

We have fabricated miniature planar IR waveguides of thickness 30–50 $\mu$m, consisting of 12-mm long, 2-mm wide strips of Ge supported on ZnS substrates. Evidence for efficient propagation of broadband IR light through these waveguides is provided by the presence of characteristic high and low frequency optical cut-offs of Ge; by the observation of an oscillatory interference pattern in the transmittance spectrum, which exhibits a dependence on waveguide thickness and propagation angle closely matching waveguide theory; and by the detection of strong evanescent-wave absorption from small (2 mm$^2$) droplets of liquid, e.g. water, on the waveguide surface. As also predicted by theory, the surface sensitivity (detected light absorbance per unit area of sample-waveguide contact) was shown to increase as a function of incidence or bevel angle.

8 Claims, 6 Drawing Sheets

SUPPORT PLANAR GERMANIUM WAVEGUIDES FOR INFRARED EVANESCENT-WAVE SENSING

CROSS-REFERENCE TO RELATED APPLICATIONS

This application claims the benefit of Provisional Patent Application Ser. No. 60/019,969, filed Jun. 17, 1996, in the names of Mark Braiman and Susan Plunkett, the disclosure of which is incorporate herein, by reference thereto, as though recited in full.

ADDITIONAL DISCLOSURES INCORPORATED BY REFERENCE.

Additional disclosure is contained in applicants' publication entitled, "Design for Supported Planar Waveguides for Obtaining Mid-IR Evanescent-Wave Absorption Spectra from Biomembranes of Individual Cells", Mark S. Braiman, and Sysan E. Plunkett, Volume 51, Number 4, April 1997, Applied Spectroscopy, copyright 1997, Society for Applied Spectroscopy, the disclosure of which is incorporated herein, by reference thereto, as though recited in full.

Another additional disclosure is contained in applicants' publication, entitled, "Mid-IR evanescent-wave absorption spectra of thin films and coatings measured with a ~50-micrometer planar Ge waveguide sensors", James J. Stone, Mark S. Braiman, and Susan E. Plunkett, published Jun. 15, 1997, Process SPIE, the disclosure of which is incorporated herein, by reference thereto, as though recited in full.

BACKGROUND OF THE INVENTION

The development of mid-infrared (IR) waveguides has been driven by their use as remote or small-sample-size chemical sensors for surface sensitive spectroscopy. Such waveguides can be thought of as miniaturized multiple reflection elements (MREs) wherein the incident light undergoes total internal reflection at the interface between media of different refractive indices. At each internal reflection within the waveguide, a portion of the optical field, the evanescent wave, extends beyond the high-index waveguide into the adjacent low-index medium, to a depth ($d_p$) dependent on the angle of incidence and the ratio of the two refractive indices.[1] The ability of molecules outside the high-index waveguide, but near its surface, to absorb energy travelling through the waveguide via this evanescent wave makes possible the phenomenon known as attenuated total reflection (ATR) or evanescent-wave spectroscopy (EWS).

In the IR region, high-refractive-index materials as Ge, Si, and KRS-5 ($Tl_2BrI$), cut and polished as prisms having trapezoidal or parallelogram cross-sections and dimensions on the order of 50×10×2 mm, are in common use for EWS measurements. These macroscopic waveguides typically have throughputs matched to commercial FTIR spectrometers, i.e. in the vicinity of 1–10 $mm^2$-stearadian. Commercially available IR fiber optics (multimode cylindrical waveguides made of, e.g., chalcogenide glass),[2,3] have more recently been used as EWS sensors.[4,5] These optical fibers typically have much lower throughputs than the prism MREs, complicating somewhat their use with commercial IR spectrometers. Nevertheless, when properly coupled to a small-area (low-noise) IR detector, fiber optics display the advantage that miniaturization allows smaller amounts ($\mu L$) of sample to be detected.[6-9] This advantage arises from the fact that, while the surface sensing area is smaller, the light experiences a larger number of reflection per unit length of waveguide, yielding a concomitant increase in evanescent path length. It would be desirable to see how far this advantage could be extended, i.e. how thin an EWS waveguide or fiber could be made. However, it becomes impractical to make a free-standing IR fiber less than ~50 $\mu m$ in diameter. Thus, we are interested in investigating the possibility of using supported thin planar waveguides for EWS applications.

Most thin planar waveguide development has been in the visible region, where low-loss transparent materials (polymers and glasses) are commercially available and easy to manipulate. Such waveguides have generally been used in conjunction with single-frequency lasers, which provide high luminosity, monochromaticity, and fine control over the launch angle, and have been used for absorption, Raman, and fluorescence analytical methods.[10-17] In contrast, IR-transmissive materials with the requisite high refractive indices and low attenuation values are either very brittle, or have not had techniques developed to allow them to be deposited (e.g. by evaporation or sputtering techniques) as uniform and well-adhered films of the desired thicknesses of 1–100 $\mu m$.[18] To our knowledge, there have been only two reports in the literature of mid-infrared transmitting planar waveguides, both utilizing monochromatic (laser) light to demonstrate coupling and guiding, rather than broadband light which is likely to be more suitable for general chemical sensing.[19,20]

Nevertheless, the same theory should describe both visible and infrared waveguides, and this theory indicates that with appropriate coupling methods it should be possible to use IR supported planar waveguides to perform broadband IR chemical sensing.[21] We have now proven this by fabricating supported planar waveguides as thin as 30 $\mu m$ with good broadband transmission, which demonstrate many of the characteristics predicted by planar waveguide theory.[22] In particular, they show a great increase in the sampling sensitivity as compared to previous evanescent-wave absorption measurements.

REFERENCES

1. Harrick N. J. Harrick. *Internal Reflection Spectroscopy*. Harrick, Ossining, N.Y., 1979.
2. BorWol91 A. Bornstein, M. Katz, A. Baram, and D. Wolfman. Attenuated total reflection spectroscopy with chalcogenide bi-tapered fibers. *Proc. SPIE*, 1591:256–262, 1991.
3. DriLes91 R. D. Driver, J. N. Downing, and G. M. Leskowitz. Evanescent-wave spectroscopy down infrared transmitting optical fibers. *Proc. SPIE*, 1591:168–179, 1991.
4. Albin95 R. S. Rogowski, J. S. Namkung, M. Hoke, and S. Albin. FT-IR optical fiber remote detection of aluminum hydroxide by evanescent wave absorption. *Appl. Spectrosc* 49, pages 1305–1310, 1995.
5. Burgess L. W. Burgess, D. S. Blair, and A. M. Brodsky. Study of analyte diffusion into a silicone-clad fiber-optic chemical sensor by evanescent wave spectroscopy. *Appl. Spectrosc.* 49, pages 1636–1645, 1995.
6. BraimWilson89 M. S. Braiman and K. J. Wilson. New FTIR techniques for studying biological membranes. In David Cameron, editor, *Proceedings of the Seventh International Conference on Fourier and Computerized Infrared Spectroscopy*, volume 1145, pages 397–399. Proc. SPIE, June 1989. Proc. 7th Int. Conf., Fairfax, Va. Jun. 19–23 1989.
7. jonas92 M. S. Braiman and R. E. Jonas. Evanescent-wave IR spectroscopy of single-bilayer membranes coated on chalcogenide fibers: Sensitivity improvements using a diamond rod coupler between fiber and source. *Chemical, Biochemical, and Environmental Fiber Sensors IV,* R. A. Liberman, ed., *SPIE* 1796, pages 402–411, 1992.

8. jonas93 R. E. Jonas and M. S. Braiman. Efficient source-to-fiber coupling method using a diamond rod: Theory and application to multimode evanescent-wave IR absorption spectroscopy. *Appl. Spectrosc.* 47, pages 1751–1759, 1993.

9. jonas/spie R. E. Jonas and M. S. Braiman. Compact source-to-fiber diamond optical coupler enhances absorbances from optical fiber evanescent-wave IR spectroscopy using a simple design. *Fiber Optic Sensors in Medical Diagnostics, SPIE* 1886, pages 9–14, 1993.

10. Saavedra95 L. Yang and S. S. Saavedra. Chemical sensors using sol-gel derived planar waveguides and indicator phases. *Anal. Chem.* 67, page 1307, 1995.

11. Reichert/flow] S. S. Saavedra and W. M. Reichert. A flow cell for mode-specific, integrated optical waveguide spectroscopy in aqueous superstrates. *Appl. Spectrosc.* 44, pages 1420–1423,1990.

12. Reichert/liquid S. S. Saavedra and W. M. Reichert. Prism coupling into polymer integrated optical waveguides with liquid superstrates. *Appl. Spectrosc.* 44, pages 1210–1217, 1990.

13. Reichert90 S. S. Saavedra and W. M. Reichert. Integrated optical attenuated total reflection spectrometry of aqueous superstrates using prsim-coupled polymer waveguides. *Anal. Chem.* 62, pages 2251–2256, 1990.

14. Reichert91 S. S. Saavedra and W. M. Reichert. In situ quantitation of protein absorption density by integrated optical waveguide attenuated total reflection spectrometry. *Langmuir* 7, pages 995–999, 1991.

15. Reichert92 W. M. Reichert, D. S. Walker, and C. J. Berry. Coming 7059, silicon oxynitride, and silicon dioxide thin-film integrated optical waveguides: In search of low loss, nonfluorescent, reusable glass waveguides. *Appl. Spectrosc.* 46, pages 1437–1441, 1992.

16. Saavedra94 N. R. Armstrong, L. Yang, S. S. Saavedra and J. Hayes. Fabrication and characterization of low-loss, sol-gel planar waveguides. *Anal. Chem.* 66, page 1254, 1994.

17. Rabolt S. Turrell J. D. Swalen C. G. Zimba, V. M. Hallmark and J. F. Rabolt. Applications of Fourier transform Raman spectroscopy to studies of thin polymer films. *J. Phys. Chem.* 94, pages 939–943, 1990.

18. vacdeposit J. M. Mir and J. A. Agostinelli. Optical thin films for waveguide applications. *J. Vac. Sci. Technol. A* 12, pages 1439–1445, 1994.

19. Siguide Vincent. Topical meeting on integrated optics. *Opt. Soc. Am.,* Washington, D.C., 1972.

20. Geguide W. S. C. Chang and K. W. Loh. Experimental observation of 10.6-micron guided wave in Ge thin films. *Appl. Opt.* 10, pages 2361–2362, 1971.

21. marcuse D. Marcuse. *Theory of Dielectric Optical Waveguides.* Academic Press, NY, 1991.

22. Schaldach K. Abraham G. Muller and M. Schaldach. Quantitative ATR spectroscopy: Some basic considerations. *Appl. Opt.* 20, pages 1182–1190, 1981.

23. griffiths P. R. Griffiths and J. A. DeHaseth. *Fourier Transform Infrared Spectroscopy.* Wiley/Interscience, NY, 1986.

24. SimhonKatz88 S. Simhony, I Schnitzer, A. Katzir, and E. M. Kosower. Evanescent wave infrared spectroscopy of liquids using silver halide optical fibers. *J. Appl. Phys.,* 64(7):3732–3734, 1988.

25. oocytespec R. E. Jonas, S. E. Plunkeft and M. S. Braiman. unpublished results. 1996.

BRIEF SUMMARY OF THE INVENTION

There are three particularly novel aspects to our fabrication and use of thin supported planar IR waveguides. First, we have generated our waveguides by physically "whittling away" at a macroscopic piece of highly transparent single-crystal Ge. rather than by attempting either to deposit or to modify chemically a thin film of transmissive material. The latter are the most common approaches for generating thin-film waveguides. For example, sputtering is the only method to have been used previously in an attempt to fabricate thin-film Ge light guides for wavelengths in the 2–10 $\mu$m range[20]. However, this attempt resulted in a waveguide with rather high attenuation of about 20 dB per cm, due to scattering from the non-uniformly-deposited Ge. It was possible to detect transmission of $CO_2$ laser light through such a waveguide. Our attempts at detecting broadband transmission through similarly-fabricated thin-film-sputtered waveguides, e.g. 1-$\mu$m thick Ge on $CaF_2$, have failed (data not shown), most likely due to the much lower luminosity of the broadband light source available to us as compared to the $CO_2$ laser used previously. We were able to succeed in obtaining IR transmission using the weaker broadband source only by developing waveguides with much lower scattering losses than currently seem to be obtainable with sputtered Ge films.

A second innovation is that we have added a "cladding" for the waveguide's supported surface, in the form of a rather thick vacuum-deposited layer of ZnS. This turns out to be crucial for fabrication and use, since it was not possible for us to attach the piece of bulk single-crystal Ge to a substrate without using IR-absorbing adhesive materials. Only by protecting the Ge with the vacuum-deposited cladding is it possible to use simple cements or optical adhesives to attach it firmly enough to allow grinding and polishing to a few-$\mu$m thickness.

Finally, the third novel aspect of our waveguide is the direct method that we use to couple light into and out of its ends. Such direct coupling is generally not used for monochromatic (e.g. laser) light; more efficient coupling methods exist (e.g. prism coupling) that depend on optical interference effects. However, use of curved mirrors with foci at the two ends of a waveguide is probably the most generally useful means of coupling a broad bandwidth of light into it. This has long been known to be true for macroscopic MREs used for EWS.[1] Based on our demonstration here, this may also be true for waveguides of arbitrarily thin dimension—with the caveat that in some thickness ranges, the waveguides may show considerable oscillations of throughput, as shown below.

DETAILED DESCRIPTION OF THE INVENTION

1. Methods for fabrication of thin supported planar Ge waveguides.

Infrared waveguides were fabricated from commercially available prisms of Ge and ZnS. The Ge prisms were purchased as 12×2×2-mm orthorhombs from Spectral Systems (Hopewell Junction, N.Y.), and were each coated on one 12×2-mm side with a 2-$\mu$m-thick layer of ZnS using chemical vapor deposition (CVD). The ZnS-coated side of each Ge prism was then cemented with polycyanoacrylate adhesive to a ZnS substrate (25×12×2-mm orthorhomb). The IR-transparent layer between the Ge waveguide and the adhesive is absolutely necessary to prevent the IR light from being completely attenuated by the strongly absorbing polycyanoacrylate. This was shown by our repeated failed attempts to transmit light through waveguides fabricated the same way but without the CVD coating on the cemented face of the Ge.

Figure 1:
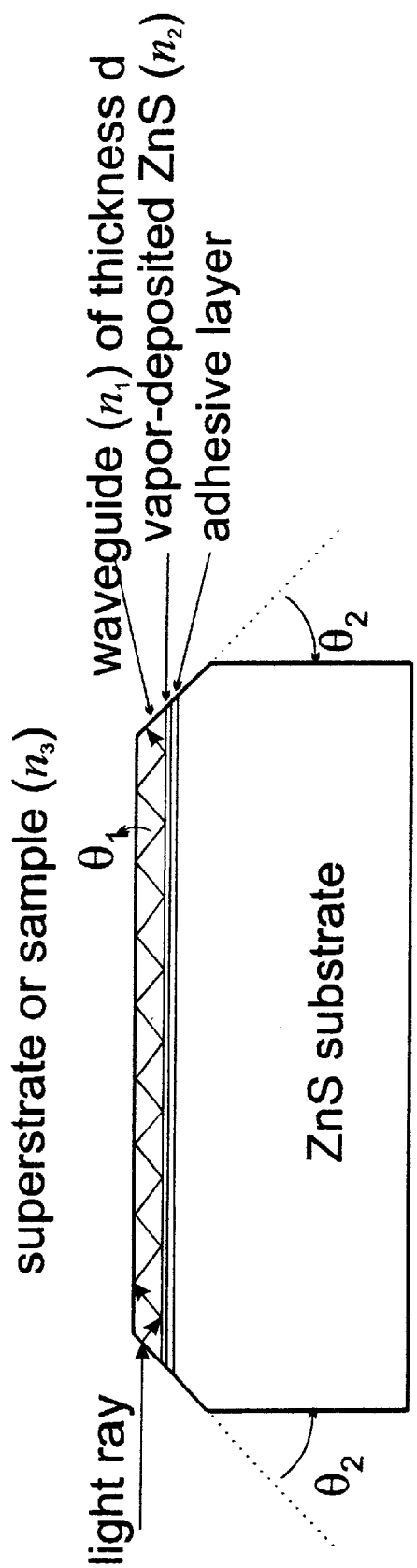
FIG. 1 Schematic of the supported planar Ge waveguide used for infrared evanescent-wave sensing. $\theta_1$ is the internal propagation angle; $\theta_2$ is the launch or bevel angle; and $n_1$, $n_2$, $n_3$ are the refractive indices of the waveguide, substrate, and superstrate, respectively. The relative thicknesses of the different layers are not to scale.
Figure 2:
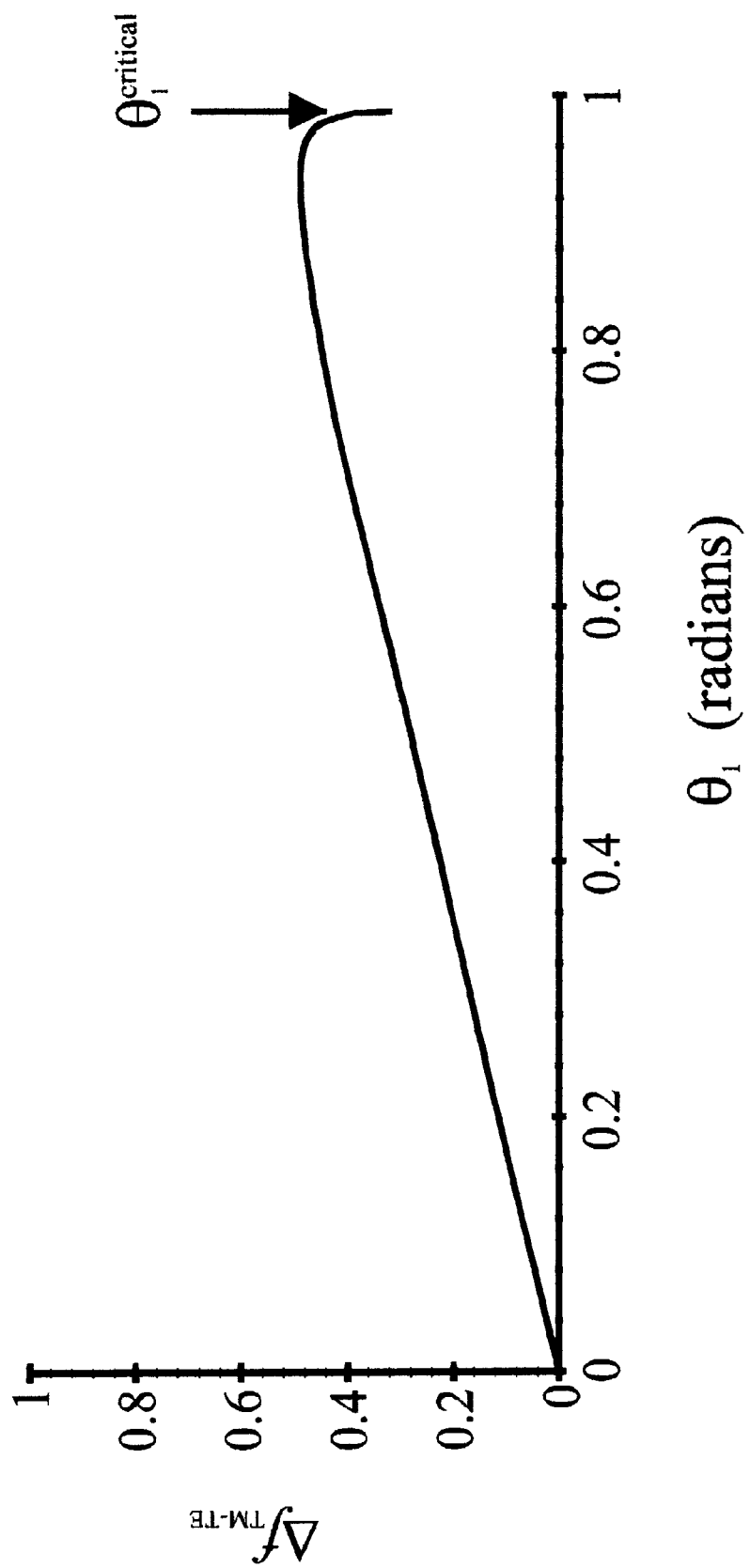
FIG. 2 The expected separation $\Delta f$TM-TE between the oscillatory transmission patterns for TE and TM modes, normalized to the common mode spacing shared by both, and plotted as a function of $\theta_1$, the internal propagation angle measured relative to the waveguide surface plane.

The 2 mm-thick supported Ge strip was then ground and polished by hand to a final thickness of 30–100 $\mu$m using the abrasive powders and flat glass polishing stone in a commercially available polishing kit (Harrick, Ossining, N.Y.). For the final steps of polishing, the abrasive powders were replaced by Al$_2$O$_3$ lapping paper. The final thickness and degree of polish of each waveguide were measured with a visible light microscope. Typically the observed random surface scratches were less than 3 $\mu$m in depth. Beveled ends were ground on the waveguide (and the substrate below) using PTFE guides cut to the desired angle, using the same lapping paper. A schematic of a typical waveguide is shown in FIG. 1.

Broadband infrared light was focused through the waveguide and measured using an IR microscope (IR-Plan™ Infrared Microscope Accessory, Spectra-Tech, Stamford, Conn.), interfaced to an FT-IR spectrometer. This IR microscope was selected because it is one of the only models available that permits the separate focusing of the objective and condenser mirrors on the input and output ends of the waveguide, some 12 mm apart. Light exiting the waveguide was collected and focused onto a photoconductive HgDcTe dectector having (0.1 mm)$^2$ active area (Graseby Infrared, Model FTIR-M16-0.10). Data processing was done with GRAMS 386 software (Galactic Industries, Salem, N.H.).

2. THEORY

Oscillations in the single-beam throughput spectrum of a planar waveguide are expected to arise from the requirement to satisfy one of the two eigenvalue equation one of the two eigenvalue equations of a planar waveguide in order to obtain transmission. For a defined thickness and propagation angle, each of these two equations (see below), which correspond to the two possible polarizations, is satisfied only at a set of evenly-spaced light frequencies. The spacing is the same for both polarizations, and is thus expected to be observed even when observing the transmission with unpolarized light.

To demonstrate this, we will start from a standard theory of planar dielectric waveguides[21], and derive expressions that relate the period of the oscillations ($\Delta\bar{v}$) in the broadband IR transmission spectrum to three experimentally fixed parameters of the waveguide: thickness d, refractive index ($n_1$), and propagation angle $\theta_1$ or bevel angle $\theta_2$ (defined by the diagram in FIG. 1). We consider our planar waveguide sensors as approximations to the well-studied asymmetric planar slab waveguide, where waveguide, substrate, and superstrate have refractive indices $n_1$, $n_2$, $n_3$, respectively. If we use the shorthand notations $n_{21}=n_2/n_1$ and $n_{31}=n_3/n_1$, then the eigenvalue equations are:

$$\tan\kappa d = \frac{\kappa(\gamma+\delta)}{\kappa^2-\gamma\delta} \text{ (for guided } TE \text{ modes)}$$

-continued $$= \frac{\kappa(n_{21}^2\gamma + n_{31}^2\delta)}{n_{21}^2 n_{31}^2 \kappa^2 - \gamma\delta} \quad \text{(for guided TM modes)}$$

The parameters $\kappa$, $\gamma$, and $\delta$ are characteristic of the mathematical solutions to Maxwell's equations in the waveguide, the substrate, and the superstrate, respectively. For waveguides that are thick compared to the wavelength of light propagating inside them, these variables can be approximated as simple functions of a well-defined propagation angle $\theta_1$. We will restrict ourselves to considering a spectral region of sufficiently short wavelength (<10 μm in vacuo, or <2.5 μm inside the Ge), compared to the waveguide thickness d (30–50 μm), that this is true. We will therefore make the substitutions $\kappa=2\pi n_1 \bar{v} \sin \theta_1$; $\gamma=2\pi\bar{v}(n_1^2 \cos^2\theta_1 - n_2^2)^{1/2}$; $\delta=2\pi\bar{v}(n_1^2 \cos^2\theta_1 - n_3^2)^{1/2}$. (What we have written so far are equations 1.3-26, 1.3-63, and 1.2-13 through 1.2-15 of Marcuse[21], with minor mathematical rearrangements).

In the Results and Discussion section below, we will make the further assumption that, because of the very high refractive index of Ge ($n_1=4.0$), the propagation angle $\theta_1$ is almost equal to the bevel angle $\theta_2$ of the ends of the waveguide, regardless of what range of angles of light are focused on the input end and collected from the output end of the waveguide. We will therefore use a value of $\theta_1$ calculated by assuming simple Snell's-law behavior for a central (axis) ray of the microscope's light-focusing mirror system, i.e. $\theta_1=\theta_2-\arcsin[\sin(\theta_2/n_1)]\cong 0.75\,\theta_2$.

We can now re-cast the eigenvalue equations in terms of the experimental parameters $\bar{v}=1/\lambda$ (the wavenumber of the light); the propagation angle $\theta_1$; and the refractive indices $n_1$, $n_2$, and $n_3$. From the resulting simplified eigenvalue equation, we wish to obtain the allowed solutions of $\bar{v}$ at externally fixed values of $\theta_1$ and d. Note that this differs from the more common approach of examining the solutions of $\theta_1$ at fixed values of $\bar{v}$ and d.

To proceed, we need only realize that the right sides of equations 1 and 2 are both independent of light frequency $\bar{v}$, since every factor of this parameter in the numerator is balanced in the denominator. Thus, the two eigenvalue equations reduce to $$\tan \kappa d \in \{E_{TE}, E_{TM}\}$$

where $$E_{TE} = \frac{\sin\theta_1 \left[(\cos^2\theta_1 - n_{21}^2)^{1/2} + (\cos^2\theta_1 - n_{31}^2)^{1/2}\right]}{\sin^2\theta_1 - (\cos^2\theta_1 - n_{21}^2)^{1/2}(\cos^2\theta_1 - n_{31}^2)^{1/2}}$$

and $$E_{TM} = \frac{\sin\theta_1 \left[n_{21}^2(\cos^2\theta_1 - n_{21}^2)^{1/2} + n_{31}^2(\cos^2\theta_1 - n_{31}^2)^{1/2}\right]}{n_{21}^2 n_{31}^2 \sin^2\theta_1 - (\cos^2\theta_1 - n_{21}^2)^{1/2}(\cos^2\theta_1 - n_{31}^2)^{1/2}}$$

are simply two constants determined by the parameters $\theta_1$, $n_1$, $n_2$, and $n_3$ for a particular waveguide geometry. The set of solutions to the simplified form of the eigenvalue equation is now easily obtained:

$$\kappa d = \arctan E + \pi N; E \in \{E_{TE}, E_{TM}\}$$

-continued $$\bar{v} = \frac{f + N}{2n_1 d \sin\theta_1}; f \in \left\{\frac{\arctan E_{TE}}{\pi}, \frac{\arctan E_{TM}}{\pi}\right\}$$

In both of the preceding equations, N is allowed to take on any integer value. That is, the allowed TE and TM frequencies are each expected to be evenly spaced, with a period of $\Delta\bar{v}=1/(2n_1 d \sin\theta_1)$. The calculated separation between the TE and TM series, $\Delta f_{TM-TE}=(\arctan E_{TE}-\arctan E_{TM})/\pi$, is expected to be 0 for $\theta_1=0$, and to increase roughly linearly with $\theta_1$, until very close to the critical angle. For the materials used by us ($n_1=4.0$, $n_2=2.2$, $n_3=1$), $\Delta f_{TM-TE}$ is plotted as a function of $\theta_1$ (in radians) in FIG. 3.

Depending on the separation between TE and TM modes, it is expected to be easier or more difficult to see their shared oscillation period in the throughput spectrum obtained with unpolarized light. At low values of $\theta_1$, where the TE and TM modes are expected to be separated by much less than a single oscillation period, they should superimpose quite well, making it easy to see an interference pattern. At values approaching the critical angle, however, the TE and TM modes are expected to be almost perfectly interleaved, leading to an apparent period that is only half of the actual period $1/(2n_1 d \sin\theta_1)$ and to a smaller-amplitude intensity oscillation that is much harder to observe on the gradually-changing throughput spectrum. This actually turns out to be quite desirable for a broadband evanescent-wave sensor.

3. Results and Discussion

Figure 3:
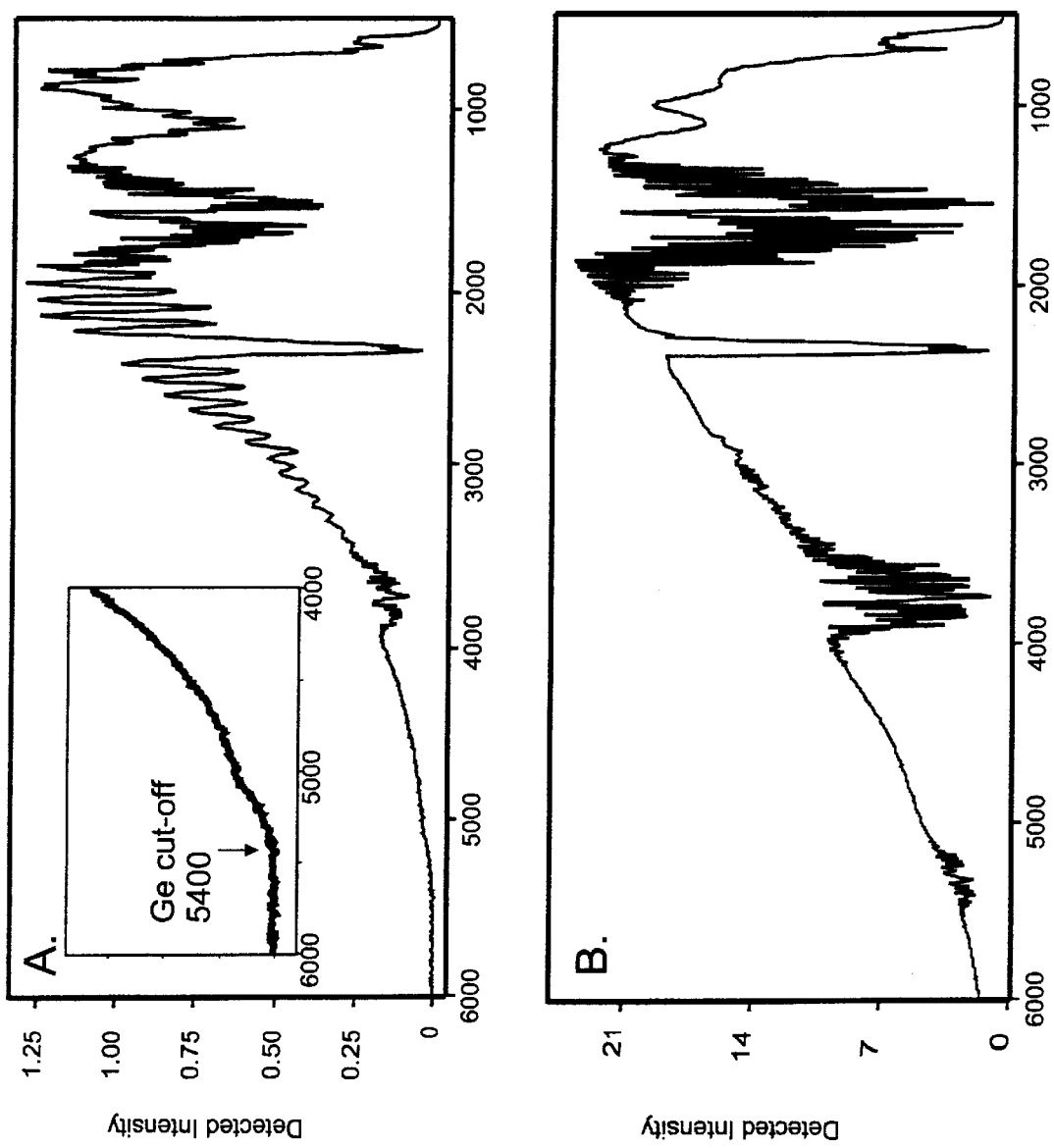
FIG. 3 The uncorrected FT-IR single-beam intensity throughput spectrum for a typical 50-$\mu$m-thick waveguide with 15° bevel angles (A), and the corresponding intensity spectrum of a rectangular aperture set to the same size as the cross-section as the waveguide (2 mm×50 $\mu$m) (B). The sharply-delineated spectral features present in both waveguide and open-beam spectra near 1650, 2200, and 3800$^{-1}$ are absorption bands due to gaseous water and carbon dioxide. These are present since the beam path in the IR microscope contained room air, (i.e., was unpurged). Inset, an expansion of the 6000–4000 cm$^{-1}$ region, clearly showing the high frequency transmission cutoff of Ge at ~5400 cm$^{-1}$.

FIG. 3 shows the uncorrected FT-IR single-beam intensity throughput spectrum for a typical 50-μm-thick waveguide with 15° bevel angles. It is compared with the open-beam throughput spectrum of the microscope through a rectangular aperture the same size as the cross-section of the waveguide (2 mm×50 μm). The most obvious novel feature in the waveguide throughput spectrum is the rapidly-oscillating beat pattern, superimposed on the normal throughput, in the 2000–3500 cm$^{-1}$ region. As discussed further below, this interference pattern corresponds closely to the mode structure predicted by waveguide theory, and is the clearest demonstration that light is being guided though the thin layer of Ge. Additionally, the waveguide shows characteristic Ge spectral high and low frequency cut-offs at 5400 cm$^{-1}$ (see inset) and 550 cm$^{-1}$.

It should also be noted that even below 5400 cm$^{-1}$, the spectral intensity transmitted through the waveguide decreases with increasing frequency much faster (relative to the maximum value near 2000 cm$^{-1}$) than in the open-beam spectrum. This drop-off is an indication of the scattering losses due to imperfections on the waveguide surface(s). The less thoroughly the surface of the waveguide was polished, the more drastic was the drop-off. It would almost certainly be possible to improve on the high frequency throughput, since commercial polishers routinely obtain better finishes on optics than we are able to obtain by hand polishing. The overall measured transmittance of our waveguide at 2000 cm$^{-1}$ is about 5% relative to an aperture of the same cross-section. We can estimate that reflection losses from the two air-Ge interfaces at the ends of the waveguide as ~50% (based on our unpublished measurements of the transmittance through a Ge window, as well as theory). Thus the waveguide has an attenuation of about 10 dB over its entire 12-mm length. This means that our 50-μm thick Ge waveguide has about 10-fold less attenuation than a 1-cm-long, 5-μm thick Ge waveguide sputtered onto a KRS-5 substrate,[21] for which the attenuation was estimated as 20 dB per cm, and through which light transmission was detected only by using a powerful $CO_2$ laser.

Figure 4:
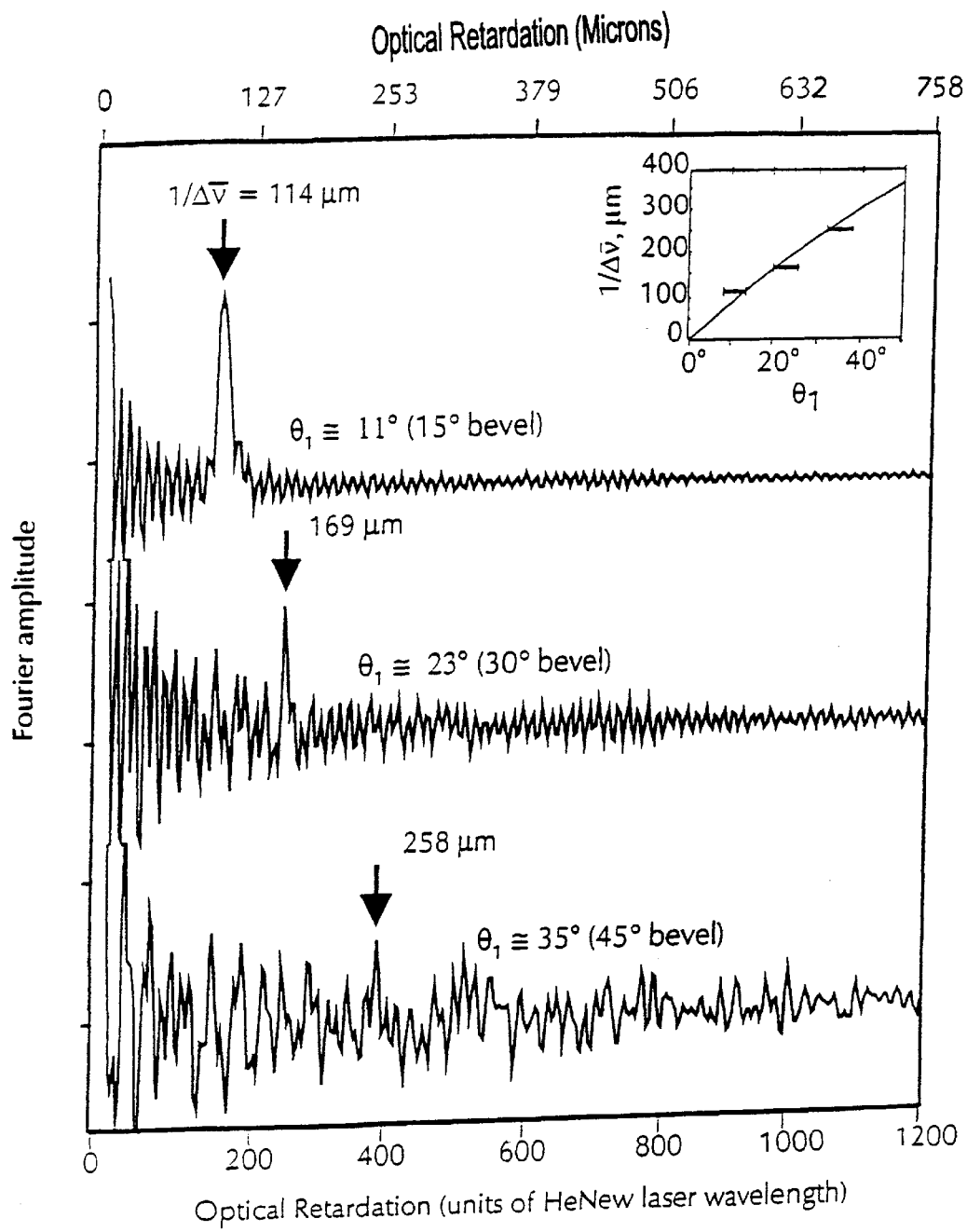
FIG. 4 Fourier tranforms of the single-beam intensity throughput of the 50-$\mu$m-thick waveguide with $\theta_2=15°$, 30°, and 45° bevels. In each, the spike feature associated with the oscillatory (beat) pattern in the spectrum is indicated with an arrow. Each spectrum, measured as in FIG. 4, was truncated at 4400 and 2430 cm$^{-1}$, then apodized using a Blackman-Harris 3-term function, and Fourier transformed. The phase was corrected to obtain just the amplitude of the Fourier transform. The 15° and 30° data were obtained with unpolarized light. However, as $\theta_1$ increases, the amplitude of the oscillatory pattern in the spectrum decreases, because the TE- and TM-mode beat patterns move "out of phase" and cancel each others' intensity (see Theory section). Therefore, data at 45° were obtained using TE-polarized light (using a wire grid polarizer). With unpolarized light at 45°, the spike in the corresponding plot is just barely visible, at nearly the same point as obtained with the TE-polarized light. Inset, plot of the reciprocal of the oscillation period ($1/\Delta\bar{v}$) versus internal propagation angle ($\theta_1$). The filled circles are experimental data and the straight line is the theoretically predicted behavior $1/\Delta\bar{v}=(2n_1 d \sin \theta_1)$ with $n_1=4.0$, $d=50$ $\mu$m, and $\theta_1=\theta_2-\arcsin[\sin(\theta_2/n_1)]$. The main source of error in this plot is imprecision in our grinding the bevel angle $\theta_2$. The error bars in the inset show the resulting $\pm 5°$ uncertainty in $\theta_1$.

FIG. 4 shows Fourier transforms of the 4400–2430 cm$^{-1}$ region of the throughput spectra for bevel angles ($\theta_2$) of 15°, 30°, and 45°. These plots provide the most precise measurement of the period of the oscillating beat pattern, since a sine wave in the spectrum corresponds to a spike in its Fourier transform. The optical retardation at this spike is just the reciprocal of the oscillation period $\Delta\bar{v}$ in the spectrum. The inset is a plot of the reciprocal of the oscillation period ($1/\Delta\bar{v}$) versus internal propagation angle ($\theta_1$). The filled circles are experimental data and the straight line is the theoretically predicted behavior using Equation (3) above for unpolarized light: $1/\Delta\bar{v}=(2n_1 d \sin\theta_1)$ with $n_1=4.0$, d=50 $\mu$m, and $\theta_1=\theta_2-$arcsin [sin ($\theta_2/n_1$)]. It is apparent that there is a close correlation between experimental and theoretical values. We observed a similar agreement with theory for the oscillations in the throughput of a 30-$\mu$m thick waveguide, at $\theta_2$ angles of 15° and 30°, only (data not shown).

Figure 5:
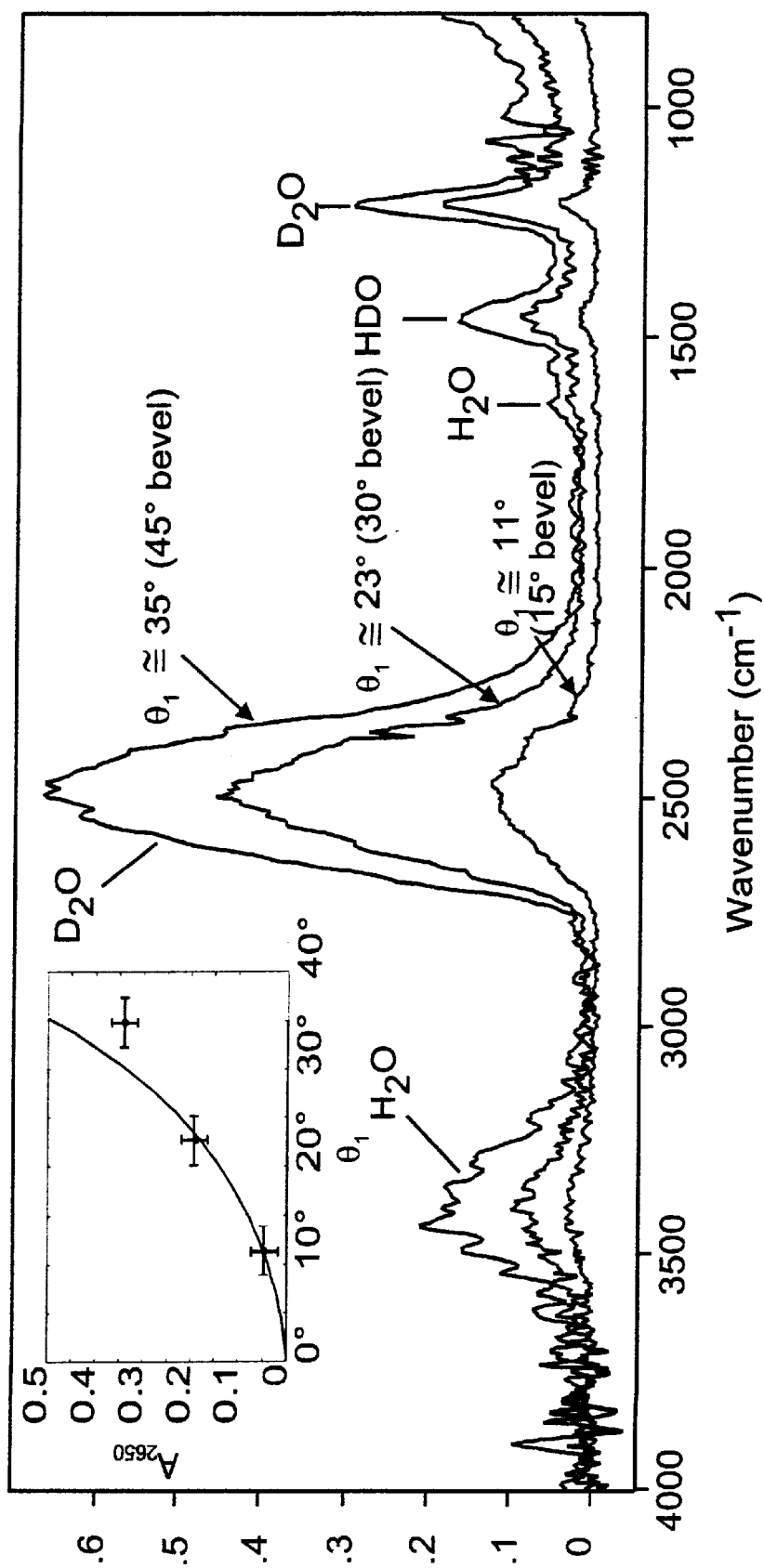
FIG. 5 FT-IR evanescent-wave absorbance spectra of a 1-$\mu$L D$_2$O droplet on the waveguide for each of the three bevel angles ($\theta_2=15°$, 30°, and 45°). Bands at ~2500 cm$^{-1}$ and 1250 cm$^{-1}$ are due to D—O stretch and DOD bend vibrations, respectively. The smaller bands at 3400 cm$^{-1}$ and 1450 cm$^{-1}$ are due to H—O stretch and H—O—D bend vibrations, and resulted from rapid H/D exchange of the droplet with H$_2$O in the room air over the course of the 30-minute measurement. The degree of exchange was similar for all 3 measurements, as was the decrease in droplet size (20%–30% over 30 min) due to evaporation. Inset, plot of the absorbance at 2650 cm$^{-1}$ versus internal propagation angle $\theta_1$. The filled circles are experimental data and the straight line is the theoretically predicted behavior for TE-modes (see text). The $A_{2650}$ values were each increased to take into account the absorbance at ~3500 cm$^{-1}$ resulting from H/D exchange. The horizontal error bars represent our estimate of $\pm 5°$ uncertainty in the bevel angle; the vertical error bars result from noise in the spectrum and uncertainty in the degree of H/D exchange.
Figure 6:
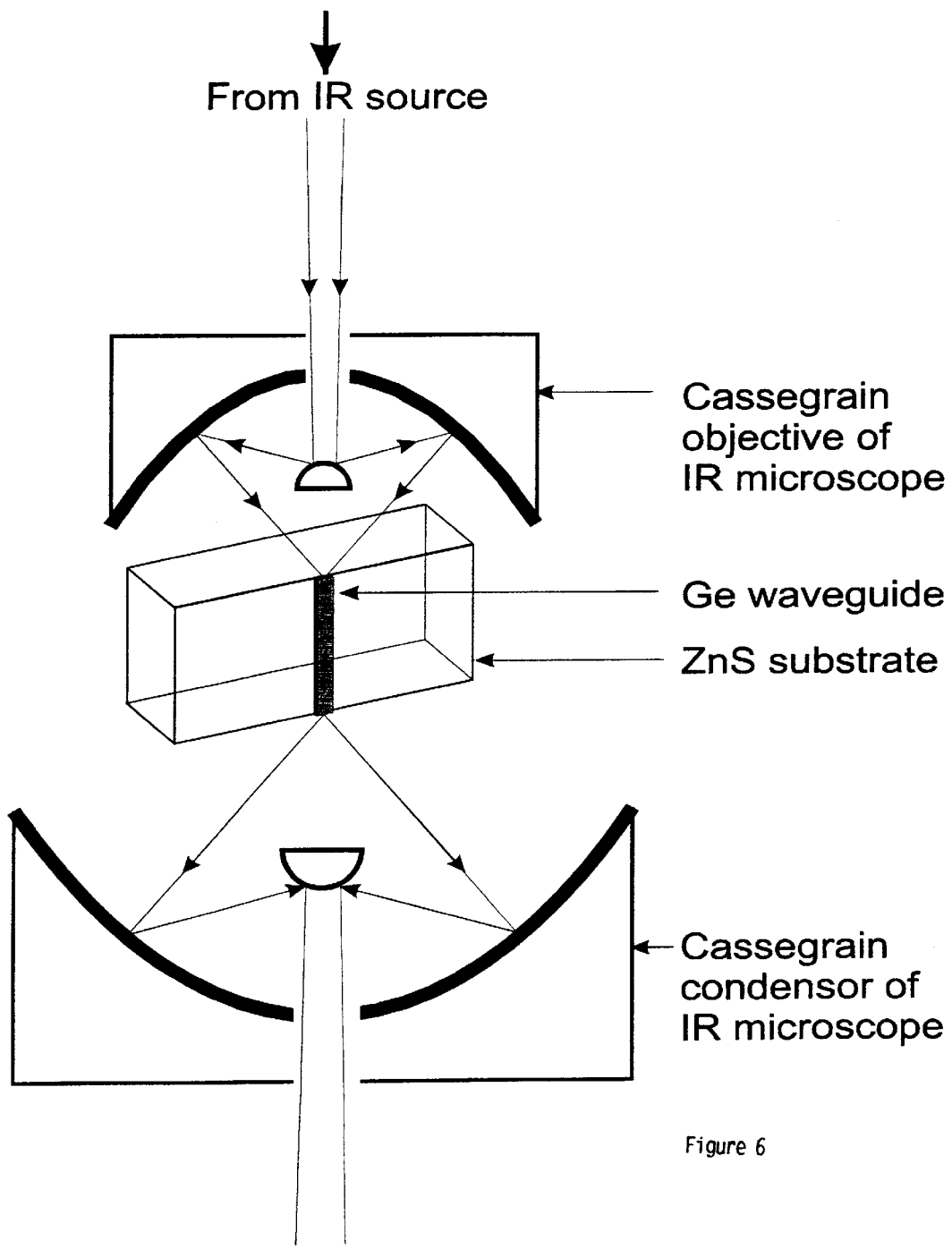
FIG. 6 A schematic representation illustrating an IR light path from the source of the IR light, through the objective of an IR microscope, through a germanium waveguide, and showing the light collected by the condensor mirror and focused onto a detector.

FIG. 5 shows absorbance spectra for a ~2 mm-diameter $D_2O$ droplet on the waveguide for each of the three bevel angles. $D_2O$ (deuterated water) was chosen since it adheres well to the waveguide, evaporates slowly, and exhibits well-known absorption bands in spectral regions unobscured by absorption due to $H_2O$ vapor. As the bevel angle increases, surface sensitivity (detected IR absorbance per unit sample contact area) also increases. This phenomenon is the result of three well-established relationships of the bevel angle ($\theta_1$) to detected intensity: (1) the evanescent field penetration depth ($d_p$) increases with $\theta_1$ up to $\theta_{critical}$; (2) the interfacial evanescent field intensity increases monotonically with $\theta_1$, up to 90°; and (3) the number of internal reflection increases monotonically with $\theta_1$. At low angles $\theta_1$, the measured absorbance is expected to be roughly a quadratic function of $\sin\theta_1$.[1] We can relate the measured IR absorbance A to known parameters of the water ($D_2O$) sample and waveguide just by multiplying the right side of Harrick's equation 2-25, which describes the coupling of the evanescent wave to an absorbing medium at a single internal reflection, by the number of internal reflections at which our $D_2O$ droplet is sensed. This number is $\tan\theta_1 \times l/2d$ (remembering that the absorbing medium is present on only one side of the waveguide). For simplicity, we assume the use of TE-polarized light. Corresponding expressions for TM-polarized or unpolarized light are somewhat more complicated but of a similar magnitude, and exhibit a roughly similar dependence on $\theta_1$.

$$A = \frac{k_3 n_{31}^2 l}{(1-n_{31}^2)d} \frac{\sin^2\theta_1}{\cos\theta_1 (\cos^2\theta_1 - n_{31}^2)^{1/2}}$$

Here $k_3$ is the imaginary refractive index of the sample (which we estimate, for $D_2O$ at ~150 cm$^{-1}$ above its 2500-cm$^{-1}$ absorption maximum, by using a published value of 0.13 for $H_2O$ at a corresponding frequency displacement from its 3350-cm$^{-1}$ absorbance maximum); $n_{31}$ is the ratio of the (real) refractive index of the sample to that of the waveguide, 0.33; l is the contact length of the $D_2O$ droplet with the waveguide surface (2.5 mm); d is the waveguide thickness (50 $\mu$m); and $\theta_1$ is the internal angle of propagation, which we varied.

The inset to FIG. 5 is a plot of IR absorbance at 2650 cm$^{-1}$ ($A_{2650}$) versus internal propagation angle ($\theta_1$). The filled circles are experimental data and the straight line is the theoretically predicted behavior. For this plot, we selected a wavenumber somewhat away from the absorbance maximum, to reduce problems due to absorbance flattening. This is a well-known phenomenon in EWS that arises due to the inaccurate assumption of only a single internal propagation angle $\theta_1$, and only a single contact length l for the roughly-circular water droplet. In fact, the use of focusing optics with large numerical aperture means that for each bevel angle $\theta_2$, light traversing the waveguide has a range of internal propagation angles $\theta_1$. Furthermore, the interaction length l is significantly shorter for light traversing the waveguide near the edges of the 3-mm-diameter droplet than for light near the center. Both of these factors mean that there is actually a range of effective path lengths through the sample in each of our measurements. This is expected to result in a sublinear dependence of absorbance on average effective path length, i.e. a non-Beer's Law type of behavior, as we actually observe. As expected, the deviation of our measured data from theoretical dependence on $\theta$ was even greater when we selected a wavenumber closer to the absorbance maximum of 2500 cm$^{-1}$ (plot not shown).

The large surface sensitivity demonstrated in FIG. 5 is a significant improvement over previous studies using optical fibers for evanescent-wave IR spectroscopy. For instance, Simhony et al.[24] achieved an absorbance of only 0.5 for the most intense band in the $H_2O$ spectrum (3350 cm$^{-1}$), using an immersion length of 65.5-mm for a 900-$\mu$m diameter silver halide ($AgCl_x Br_{1-x}$) fiber optic in water. The same absorbance value (0.5) was obtained for a 70-mm length of 500-$\mu$m diameter chalcogenide fiber,[7] using a different coupling method that resulted in a different set of propagation angles $\theta_1$ than in the silver halide fiber experiment cited. The vast increase in sensitivity in the current study is due to the thinness (d) of the waveguide, as well as the ability to polish its supported ends at a bevel angle ($\theta_2$) of up to 45°. As mentioned above, the number of internal reflections per unit length varies as $\tan\theta_2/d$. Therefore, a 10-fold reduction in thickness (500 $\mu$m to 50 $\mu$m), and an increase of $\theta_2$ from 10–15° maximum for a free-standing fiber to 45–50° for our supported waveguide, has yielded over a 30-fold decrease in the sample contact length required to obtain an absorbance reading of 0.5.

4. Conclusion

We have fabricated the thinnest planar slab waveguides to date capable of evanescent-wave sensing in the mid-IR. When coupled to an IR microscope, these evanescent-wave sensors show a substantial improvement in surface sensitivity over thicker waveguides and fibers. Further modifications in the waveguide design and fabrication procedure are predicted to increase the surface sensitivity. These include gradually bi-tapering the waveguide by a factor of 4 or more in both its width and thickness. This will permit an even larger fraction of the guided light energy to be propagated as an evanescent wave at the waveguide's thinnest region, where is where the sensing of microscopic samples should take place. Tapering in this manner, rather than uniformly reducing the waveguide thickness, is a means of allowing more efficient coupling of light by the IR microscope into and out of all of the allowed modes of the thinnest region of the waveguide. A finer optical polish of the Ge surfaces will also enhance the detectivity by increasing the throughput.

While we have demonstrated its utility for measuring IR absorption spectra with broadband light, our waveguide design should also be useful for making sensors based on monochromatic (e.g. laser) light. These sensors should be useful for the study of very small samples, such as the membranes of single living cells.[25]

What is claimed is:

1. A miniature planar waveguide for use in detecting mid-IR evanescent-wave absorption spectra from individual cell membranes, said waveguide being a polished IR-transparent member cemented to a substrate, said IR-transparent member having a surface coating of a cladding, said cladding being a chemically vapor deposited layer of an IR-transparent material, said layer being from about 1 to about 5 microns in thickness and having a lower refractive index than that of said IR-transparent member, said step of coating a surface of said IR-transparent member with a cladding, preceding said step of cementing said IR-transparent member to a substrate, said cladding being between said IR-transparent member and said substrate.

2. The miniature planar waveguide of claim 1, wherein said IR-transparent member is germanium.

3. The miniature planar waveguide of claim 1, wherein said cladding comprises a chemically vapor deposited member selected from the group consisting of ZnS and ZnSe chemically vapor deposited on said IR-transparent material.

4. The miniature planar waveguide of claim 1, wherein said cladding comprises a chemically vapor deposited member selected from the group consisting of ZnS and ZnSe chemically vapor deposited on said IR-transparent material.

5. The miniature planar waveguide of claim 1, wherein said IR-transparent member is germanium.

6. The miniature planar waveguide of claim 1, wherein said waveguide has a final thickness of from about 30 to about 50 mircrometers.

7. The miniature planar waveguide of claim 1, wherein said waveguide is positioned within an IR-transmitting microscope, said IR-transmitting microscope having objective and condensing lenses, said IR-transmitting waveguide being positioned between said objective and condensing lenses, said objective and condensing lenses each being focused on the end surfaces of said waveguide.

8. The miniature planar waveguide of claim 7, further comprising a photoconductive detector positioned to receive IR light.

* * * * *